United States Patent [19]

Dansereau et al.

[11] Patent Number: 5,032,406
[45] Date of Patent: Jul. 16, 1991

[54] DUAL-ACTION TABLET

[75] Inventors: Richard J. Dansereau, Sherburne; Michael J. Kane, Norwich, both of N.Y.

[73] Assignee: Norwich Eaton Pharmaceuticals, Inc., Norwich, N.Y.

[21] Appl. No.: 314,672

[22] Filed: Feb. 21, 1989

[51] Int. Cl.$^5$ ............................................. A61K 9/24
[52] U.S. Cl. ..................................... 424/472; 424/471; 424/464; 424/465
[58] Field of Search ............... 424/471, 472, 464, 465

[56] References Cited

U.S. PATENT DOCUMENTS

| | | | |
|---|---|---|---|
| 2,887,438 | 5/1959 | Cooper et al. | 167/82 |
| 2,951,792 | 9/1960 | Swintosky | 424/472 |
| 3,558,768 | 1/1971 | Klippel | 424/21 |
| 4,341,759 | 7/1982 | Bogentoft et al. | 424/21 |
| 4,756,911 | 7/1988 | Drost et al. | 424/472 X |

FOREIGN PATENT DOCUMENTS 1233055  5/1971  United Kingdom ............... 424/472

*Primary Examiner*—Thurman K. Page
*Assistant Examiner*—D. Gabrielle Phelan
*Attorney, Agent, or Firm*—David L. Suter; Karen F. Clark; Jack D. Schaeffer

[57] ABSTRACT

The present invention provides a dual-action tablet composition comprising:
(a) an outer tablet comprising a first dose of active ingredient dispersed in a pH independent hydrophilic polymer matrix; and
(b) an inner tablet comprising a second dose of active ingredient in a rapidly disintegrating excipient base.

This dual-action tablet is especially efficacious for those active ingredients which have half lives of less than two hours and which experience decreased absorption efficiency in the lower gastrointestinal tract. Among the preferred dual-action tablet compositions is one wherein the active ingredient in both the inner and outer tablets is guaifenesin. Upon administration, the outer tablet provides a controlled release of the active ingredient while the inner tablet gives a second dose of active ingredient after the outer tablet has partially dissolved.

3 Claims, No Drawings

DUAL-ACTION TABLET

BACKGROUND OF THE INVENTION

This invention relates to a table-within-a-tablet pharmaceutical composition (hereinafter referred to as a dual-action tablet). The dual-action tablet gives a sustained dose of active ingredient followed by an immediate dose of active ingredient.

Depending upon the desired route of administration of the active material, pharmaceutical tablets may be produced in a variety of dosage forms that will either delay or prolong the release of the active material. The pharmacological effect of an active ingredient is typically correlated to its concentration in blood plasma of the organism. The dosage form determines how rapidly the active ingredient is released. In turn, the rate of release of active ingredient influences its blood plasma concentration. Optimal treatment often necessitates that a certain minimum effective concentration be maintained, at which concentration the active ingredient is able to exert its desired pharmacological effect on the organism. Ordinary capsules and tablets rapidly release the active ingredient, leading initially to a highly elevated concentration in plasma. However, the more quickly the active ingredient is eliminated from the organism's system, the more frequently must the active ingredient be administered to maintain the minimum effective concentration.

Many pharmaceutical compositions have been designed attempting to either prolong or delay the release of active ingredient in order to maintain a minimum effective concentration. A sustained release tablet is one which gives a continual release of drug from the time of administration. A delayed release tablet provides for a delay between the time of administration of active ingredient and its release.

The typical delayed release tablet dosage form uses enteric coated polymer systems to coat the tablet or capsule. However, the use of such pH dependent polymers in the enteric coating results in a dosage form that tends to perform erratically in humans due to variations in both gastric emptying times and the pH of gastric and intestinal fluid. Despite this, delayed release compositions may offer advantages, including: reducing the dosing regimen, reducing side effects, and targeting that portion of the alimentary canal in which the active ingredient will be released.

In contrast to delayed release tablets, sustained release tablets extend the duration of drug level in the body. Many different names are associated with sustained release products, such as timed release and prolonged release. Typical sustained release formulations are coated tablets containing an active in a polymeric matrix or coated granules of the active contained in capsules. Some of these dosage forms are designed to release portions of the active at different places in the gastrointestinal tract. Other sustained release compositions slowly dissolve or erode, allowing a gradual release of active. Sustained release compositions may offer the following therapeutic advantages: reducing side effects, reducing drug accumulation with chronic dosing, and reducing fluctuations in drug level.

Many delayed release and substained release formulations are described in the pharmaceutical literature. For example, U.S. Pat. No. 3,558,768 issued Jan. 26, 1971 describes a sustained release tablet while U.S. Pat. No. 2,887,438 issued May 19, 1959 describes a tablet alleged to have the combined properties of both delayed release and sustained release.

A disadvantage of some delayed release and/or sustained release formulations is that for active ingredients that are water soluble and have half lives of less than about two hours, it is difficult to maintain the minimum effective concentration of active ingredient in the blood plasma for a period longer than about eight hours after administration. (As used herein, the term "half life" means the time taken to decrease the concentration of drug in the blood plasma of the organism by about one half.) This may preclude a more convenient twice-a-day dosage regimen for an active material. Another disadvantage, particularly for compositions that rely upon enteric coatings for sustained or delayed release, is that the release of active ingredient may depend on the pH of the gastrointestinal environment. This may lead to erratic and unpredictable release of the active ingredient.

SUMMARY OF THE INVENTION

The present invention provides a dual-action tablet composition comprising:

(a) an outer tablet comprising a first dose of active ingredient dispersed in a pH independent hydrophilic polymer matrix; and (b) an inner tablet comprising a second dose of active ingredient in a rapidly disintegrating excipient base.

This dual-action tablet is especially efficacious for those active ingredients which have half lives of less than two hours and which experience decreased absorption efficiency in the lower gastrointestinal tract. Among the preferred dual-action tablet compositions is one wherein the active ingredient in both the inner and outer tablets is guaifenesin.

This dual-action tablet is to be contrasted with repeat-action tablets which give an immediate dose followed by a sustained dose. The present dual-action tablet has the sustained release property of providing a continual release of drug from the time of administration coupled with the delayed release property of delaying the release of a second dose of drug to some time after administration.

This allows the composition of the present invention to maintain a minimum effective concentration of active ingredient for a twelve-hour period after administration of the active ingredient. Further, the release of active ingredient is not dependent on the pH of the gastrointestinal environment in which the dual-action tablet is located. This pH independent release insures release at a certain time, irrespective of the location of the dual-action tablet in the gastrointestinal tract.

DESCRIPTION OF THE INVENTION

The compositions of the present invention contain one or more active ingredients in a dual-action tablet containing a pH independent hydrophilic polymer matrix in the outer tablet and a rapidly disintegrating core in the inner tablet.

In addition, the compositions of the present invention may contain optional pharmaceutically-acceptable components which may modify their physical characteristics and/or therapeutic effects. All components of the present composition must be pharmaceutically-acceptable. As used herein, a "pharmaceutically-acceptable" component is one which is suitable for use with humans and/or other animals without undue adverse side effects (such as toxicity, irritation and allergic response) commensurate with a reasonable benefit/risk ratio.

In particular, the present invention provides a dual-action tablet composition comprising:
(a) an outer tablet comprising a first dose of active ingredient dispersed in a pH independent hydrophilic polymer matrix; and
(b) an inner tablet comprising a second dose of active ingredient in a rapidly disintegrating excipient base.

Preferably, the weight ratio of inner to outer tablet is from about 1:2 to about 1:10. More preferably, the ratio of inner to outer tablet is from about 1:2 to about 1:5, particularly when the active ingredient in the inner tablet is the same as that in the outer tablet. Even more preferred, the ratio of inner to outer tablet is from 1:3 to 1:4, particularly when the active ingredient in both inner and outer tablets is guaifenesin.

Compositions of the present invention comprise an inner tablet composition and an outer tablet composition wherein the inner tablet is surrounded on its outer surface by the inner surface of the outer tablet. The outer tablet contains the first dose of active ingredient in a pH independent hydrophilic matrix. The outer surface of the outer tablet is in immediate contact with gastrointestinal fluid which causes the matrix to hydrate, swell and form a gel network. Release of the first dose of active ingredient in the outer tablet is preferably sustained for from about four to about eight hours. Once the outer tablet has partially dissolved, leaving a loose gel network, gastrointestinal fluid wets the inner tablet. This causes the inner tablet to swell, disintegrate and rupture the remaining gel network of the outer layer. This results in the delivery of a second dose of the active ingredient from the inner tablet at some designated time after administration.

ESSENTIAL COMPONENTS

Active Ingredient

The tablet composition of the invention contains an active ingredient in both the inner tablet (the "second dose") and the outer tablet (the "first dose") in a unit dosage form. As used herein, a "unit dosage form" is a composition of this invention containing an amount of active ingredient that is suitable for administration in a single dose to a human or lower animal subject according to good medical practice. As used herein, "active ingredient" is any chemical compound intended to have a physiological effect on the human or lower animal to whom the compound is administered. The first dose active ingredient in the outer layer may be the same as or different from the second dose active ingredient in the inner layer.

Since this invention increases the concentration of an active ingredient via a rapid-release second dose, this invention is of particular benefit for those active ingredients which have half lives of less than two hours and for which little or no absorption occurs in the intestine if the concentration decreases below a certain concentration gradient. Preferably, such a concentration-dependent active ingredient comprises both the first dose active and the second dose active. Concentration-dependent active ingredients particularly useful in the formulation of the present invention include, for example, guaifenesin, nitrofurantoin, Vitamin C, potassium chloride, quinidine sulfate, quinidine gluconate, nicotinic acid, procainamide, alprenolol, propanolol, indomethacin, isosorbide dinitrate, nitroglycerin, pseudoephedrine, prazosin, meperidine, aspirin and phendimetrazine. A preferred active ingredient is guaifenesin.

Compositions may optionally contain more than one active ingredient in either the inner or outer tablet. When guaifenesin is the active ingredient, phenylpropanolamine is preferred as an optional additional active ingredient. A particularly preferred composition is one where both the inner and outer tablet contain both guaifenesin and phenylpropanolamine.

pH Independent Hydrophilic Polymer Matrix

The outer tablet of this invention contains a "pH independent hydrophilic polymer matrix", i.e., a composition that forms a gel that dissolves and erodes due to mechanical agitation and chemical breakdown within from about 4 hours to about 8 hours after ingestion, irrespective of the pH of the specific location of the composition in the gastrointestinal tract of the subject to whom the tablet is administered.

The pH independent hydrophilic polymer matrix preferably comprises:
(a) a hydrophilic polymer material at a level of from about 10% to about 50% (by weight of the outer tablet); and
(b) a lubricant at a level of from about 0.1% to about 5% (by weight of the outer tablet).

Preferably the hydrophilic polymer material is present at a level of from about 20% to about 50%. Also preferably, the lubricant is present at a level of from about 0.1% to about 2%.

Polymer materials, lubricants and optional materials among those useful in the matrix are described in *Handbook of Pharmaceutical Excipients* (1986), incorporated by reference herein. Preferably, the polymer material is selected from the group consisting of: cellulose ethers, polyvinylpyrrolidone, mixtures of natural hydrophilic gums (such as guar gum, gum Karaya, gum tragacanth, and xanthan gum), and mixtures thereof. Preferred are hydroxypropylmethylcellulose and mixtures of two or more cellulose ethers selected from the group consisting of methylcellulose, carboxypropylcellulose, hydroxypropylcellulose, and sodium carboxymethylcellulose and mixtures thereof. Particularly preferred are the hydroxypropylmethylcellulose series of polymers, such as hydroxypropylmethylcellulose E4MCR (manufactured by Dow Chemical Company) and hydroxypropylmethylcellulose K4M.

Lubricants useful in the matrix include, for example, magnesium stearate, zinc stearate, calcium stearate, stearic acid, hydrogenated vegetable oils, sodium stearyl fumarate, glyceryl palmitostearate, glyceryl behenate, sodium benzoate, sodium lauryl sulfate, magnesium lauryl sulfate, mineral oil, talc and mixtures thereof.

In addition to the first dose of active ingredient, polymer material, and lubricant, the pH independent hydrophilic polymer matrix may contain optional fillers, pigments and dyes. Such fillers include, for example, lactose, sucrose, dextrose, mannitol, sorbitol, whey, dibasic calcium phosphate, tribasic calcium phosphate, calcium sulfate and mixtures thereof. Such dyes and pigments include those normally used in the pharmaceutical industry.

Rapidly Disintegrating Excipient Base

The inner tablet of the present invention contains a second dose of active ingredient in a "rapidly disintegrating matrix", i.e., a composition that disintegrates within from about 5 to about 10 minutes when exposed to the internal environment of the gastrointestinal tract.

The rapidly disintegrating excipient base preferably comprises:

(a) a disintegrant at a level from about 1% to about 15% (by weight of said inner tablet); and
(b) a lubricant at a level from about 0.1% to about 2% (by weight of said inner tablet).

Disintegrants, lubricants and optional materials among those useful in the base are described in *Handbook of Pharmaceutical Excipients* (1986), incorporated by reference herein. Disintegrants useful in the base include, but are not limited to: sodium starch glycolate, preferably at a level from about 2% to about 6%; croscarmellose sodium, preferably at a level from about 2% to about 10%; crospovidone, preferably at a level from about 2% to about 15%; starch, preferably at a level from about 3% to about 30%; pregelatinized starch, preferably at a level from about 5% to about 20%; microcrystalline cellulose, preferably at a level from about 5% to about 30%; alginic acid, preferably at a level from about 2.5% to about 20%; amberlite ion exchange resins, preferably at a level from about 1% to about 6%; polyvinylpyrrolidone, preferably at a level from about 1% to about 10%; soy polysaccharides, preferably at a level from about 10% to about 30%; sodium carboxymethylcellulose, preferably at a level from about 1% to about 10%; and mixtures thereof.

Lubricants useful in the base include, for example, magnesium stearate, zinc stearate, calcium stearate, stearic acid, hydrogenated vegetable oils, sodium stearyl fumarate, glyceryl palmitostearate, glyceryl behenate, sodium benzoate, sodium lauryl sulfate, magnesium lauryl sulfate, mineral oil, talc and mixtures thereof.

In addition to the second dose of active ingredient, disintegrant and lubricant, the rapidly disintegrating excipient base may contain fillers and binders. Such fillers include lactose, sucrose, dextrose, mannitol, sorbitol, whey, dibasic calcium phosphate, tribasic calcium phosphate and calcium sulfate.

Such optional binders include methylcellulose, preferably at a level from about 1% to about 3%; sodium carboxymethylcellulose, preferably at a level from about 1% to about 6%; hydroxypropylmethylcellulose, preferably at a level from about 2% to about 5%; alginic acid, preferably at a level from about 1% to about 3%; ethyl cellulose, preferably at a level from about 1% to about 3%; and zein, preferably at a level of about 30%. More preferred binders include acacia, preferably at a level of about 5%; gelatin, preferably at a level from about 1% to about 3%; pregelatinized starch, preferably at a level from about 5% to about 10%; sucrose syrup, preferably at a level from about 3% to about 5%; polyvinylpyrrolidone, preferably at a level from about 1% to about 3%; and guar gum, preferably at a level from about 1% to about 10%.

Some of the optional binder materials useful in the rapidly disintegrating excipient base may also be useful as disintegrants, depending upon the level at which such materials are used and the physical and chemical properties of the second dose active ingredient. Accordingly, such materials and their levels may be selected by one of average skill in the art, to be used either as a disintegrant or a binder, depending on the physical and chemical properties of the second dose active ingredient, especially its solubility. In general, when the second dose active ingredient is water soluble and is present at levels above about 50% or more, a binder that has disintegrant properties will not perform as a disintegrant.

METHODS

The dual-action tablet is made by tableting methods known in the pharmaceutical arts. Typically, these tablets are made by a one-machine or two-machine method. In the two-machine method the mixture of ingredients that comprises the outer tablet is compressed around an inner tablet previously formed on another tableting machine. The Colton Model 232 (manufactured by Vector Corporation) is an example of a compression coating tablet press that compresses an outer tablet around an inner tablet made on another machine. In the one-machine method, a compression coating tablet press such as the Manesty DryCota Model 900 (manufactured by Manesty) compresses the rapidly disintegrating excipient base materials into a core tablet and then immediately compresses the ingredients that comprise the outer tablet around the newly formed core.

The following are non-limiting examples of compositions and methods for the manufacture of the dual-action tablet.

EXAMPLE I

A tablet composition, according to the present invention, is made comprising the following components:

| INNER TABLET | | |
|---|---|---|
| Ingredient | Per Tablet | % by Weight of Inner Tablet |
| Guaifenesin | 175.0 mg | 68.1 |
| Microcrystalline Cellulose | 35.1 mg | 13.6 |
| Crosspovidone | 35.0 mg | 13.6 |
| Polyvinylpyrrolidone | 7.3 mg | 2.9 |
| Talc | 2.3 mg | 0.9 |
| Zinc Stearate | 2.3 mg | 0.9 |
| | 257.0 mg | |

| OUTER TABLET | | |
|---|---|---|
| Ingredient | Per tablet | % by Weight of Outer Tablet |
| Guaifenesin | 425.0 mg | 70.8 |
| Hydroxypropyl-methylcellulose K4M | 139.9 mg | 23.3 |
| Stearic acid | 30.0 mg | 5.0 |
| Zinc Stearate | 5.4 mg | 0.9 |
| | 600.3 mg | |

The inner tablet is made by oscillating guaifenesin and half of the polyvinylpyrrolidone through a 30 mesh screen. The blend is then transferred to a pharmaceutical grade blender and mixed until it is of uniform consistency. It is then granulated with polyvinylpyrrolidone that had been previously dissolved in a sufficient amount of purified water to make a solution of from about 8% to about 12% of polyvinylpyrrolidone. This mixture is discharged and dried in a forced air oven at 40° C. until the water content is less than 1%. The dried granulation is then oscillated through a 12 mesh screen and returned to the blender. The remaining polyvinylpyrrolidone, microcrystalline cellulose and talc are added to this dried granulation and mixed until it is of uniform consistency. Finally, zinc stearate is added and the mixture is mixed until it is of uniform consistency. This mixture is then compressed into inner tablets using a standard tableting press.

The outer tablet is made by first passing guaifenesin through an oscillator equipped with a 30 mesh screen. After this step, the guaifenesin is transferred to a blender and hydroxypropylmethylcellulose K4M and stearic acid are added to it. It is mixed until uniform. Zinc stearate is added and the mixture is blended until uniform. The mixture of ingredients that comprise the outer tablet is compressed around the already formed inner tablet, on a standard compression coating tablet press.

This composition is administered to a human being afflicted with cough or cold and acts as an expectorant.

EXAMPLE II

A composition, according to the present invention, is made comprising:

| INNER TABLET | | |
|---|---|---|
| Ingredient | Per Tablet | % by Weight of Inner Tablet |
| Guaifenesin | 200.0 mg | 77.9 |
| Phenylpropanolamine HCl | 35.0 mg | 13.7 |
| Sodium Starch Glycolate | 8.0 mg | 3.1 |
| Crospovidone | 8.0 mg | 3.1 |
| Polyvinylpyrrolidone | 3.0 mg | 1.1 |
| Magnesium Stearate | 3.0 mg | 1.1 |
| | 257.0 mg | |

| OUTER TABLET | | |
|---|---|---|
| Ingredient | Per tablet | % by Weight of Outer Tablet |
| Guaifenesin | 400.0 mg | 66.7 |
| Phenylpropanolamine HCl | 40.0 mg | 6.7 |
| Hydroxypropylmethyl-cellulose E4MCR | 150.0 mg | 25.0 |
| Talc | 5.0 mg | 0.8 |
| Magnesium Stearate | 5.0 mg | 0.8 |
| | 600.0 mg | |

The composition is made by a method essentially similar to that in Example I. The composition is administered to a human being afflicted with sinusitis and/or bronchitis and provides symptomatic relief.

EXAMPLE III

A composition, according to the present invention, is made comprising:

| INNER TABLET | | |
|---|---|---|
| Ingredient | Per Tablet | % by Weight of Inner Tablet |
| Potassium Chloride | 200.0 mg | 85.9 |
| Alginic Acid | 15.0 mg | 6.4 |
| Gelatin | 10.0 mg | 4.3 |
| Sodium Lauryl Sulfate | 4.0 mg | 1.7 |
| Calcium Stearate | 4.0 mg | 1.7 |
| | 233.0 mg | |

OUTER TABLET

-continued

| Ingredient | Per tablet | % by Weight of Outer Tablet |
|---|---|---|
| Potassium Chloride | 400.0 mg | 58.0 |
| Sodium Carboxymethyl-cellulose | 125.0 mg | 18.1 |
| Methylcellulose | 125.0 mg | 18.1 |
| Stearic Acid | 30.0 mg | 4.4 |
| Glyceryl Behenate | 10.0 mg | 1.4 |
| | 690.0 mg | |

The composition is made by a method essentially similar to that in Example I. The composition is administered to a human being as a potassium supplement.

EXAMPLE IV

A composition, according to the present invention, is made comprising:

| INNER TABLET | | |
|---|---|---|
| Ingredient | Per Tablet | % by Weight of Inner Tablet |
| Procainamide HCl | 100.0 mg | 53.5 |
| Compressible Sugar | 50.0 mg | 26.7 |
| Pregelatinized Starch | 10.0 mg | 5.3 |
| Microcrystalline Cellulose | 20.0 mg | 10.7 |
| Sodium Stearyl Fumarate | 3.5 mg | 1.9 |
| Magnesium Stearate | 3.5 mg | 1.9 |
| | 187.0 mg | |

| OUTER TABLET | | |
|---|---|---|
| Ingredient | Per tablet | % by Weight of Outer Tablet |
| Procainamide HCl | 400.0 mg | 50.0 |
| Gum Tragacanth | 180.0 mg | 22.5 |
| Xanthan Gum | 180.0 mg | 22.5 |
| Sucrose | 20.0 mg | 2.5 |
| Talc | 10.0 mg | 1.25 |
| Magnesium Stearate | 10.0 mg | 1.25 |
| | 800.0 mg | |

The composition is made by a method essentially similar to that in Example I. The composition is administered to a human being as a cardiac antiarrhythmic.

What is claimed is:

1. A dual-action tablet composition comprising:
   (a) an outer tablet comprising a first dose of guaifenesin and phenylpropanolamine HCl dispersed in a pH independent hydrophilic polymer matrix; and
   (b) an inner tablet comprising a second dose of guaifenesin and phenylpropanolamine HCl in a rapidly disintegrating excipient base.

2. A dual-action tablet according to claim 1 wherein the pH independent hydrophilic polymer matrix contains hydroxypropylmethylcellulose at a level of from about 20% to about 50% by weight of the outer tablet.

3. A dual-action tablet according to claim 2 wherein said inner tablet contains polyvinylpyrrolidone at a level of from about 1% to about 5% by weight of the inner tablet.

* * * * *